(12) United States Patent
Juhn et al.

(10) Patent No.: US 12,733,874 B2
(45) Date of Patent: Sep. 15, 2026

(54) BIO-SIGNAL MEASUREMENT DEVICE ATTACHABLE TO AND DETACHABLE FROM VARIOUS BODY-WEARABLE/BODY-ATTACHABLE PRODUCTS AND CONTROL METHOD THEREOF

(71) Applicant: Wellysis Corp., Seoul (KR)

(72) Inventors: Young Juhn, Seoul (KR); Rick Hongryul Kim, Seoul (KR); Jong Woo Kim, Seoul (KR); Jung Soo Kim, Seoul (KR); Byung Ki Moon, Seoul (KR)

(73) Assignee: Wellysis Corp., Seoul (KR)

( * ) Notice: Subject to any disclaimer, the term of this patent is extended or adjusted under 35 U.S.C. 154(b) by 349 days.

(21) Appl. No.: 18/391,838

(22) Filed: Dec. 21, 2023

(65) Prior Publication Data

US 2024/0366151 A1 Nov. 7, 2024

(30) Foreign Application Priority Data

May 4, 2023 (KR) ........................ 10-2023-0058682

(51) Int. Cl.
*A61B 5/00* (2006.01)
*A61B 5/0205* (2006.01)
*A61B 5/256* (2021.01)

(52) U.S. Cl.
CPC .......... *A61B 5/6804* (2013.01); *A61B 5/0205* (2013.01); *A61B 5/256* (2021.01);
(Continued)

(58) Field of Classification Search
CPC ..... A61B 5/6804; A61B 5/0205; A61B 5/256; A61B 2560/0204; A61B 2560/0443;
(Continued)

(56) References Cited

U.S. PATENT DOCUMENTS

2014/0296651 A1* 10/2014 Stone ........................ A61B 5/08 600/301
2015/0342269 A1* 12/2015 Oleson ................. A61B 5/6823 439/37
(Continued)

FOREIGN PATENT DOCUMENTS

KR 10-1791171 B 11/2017
KR 10-2019-0124224 A 11/2019
(Continued)

OTHER PUBLICATIONS

Office Action dated May 1, 2025, issued in counterpart Korean patent application No. 10-2023-0058682 with English translation. (17 pages).

(Continued)

*Primary Examiner* — Eugene T Wu
(74) *Attorney, Agent, or Firm* — WHDA, LLP

(57) ABSTRACT

Disclosed is a bio-signal measurement device. The device includes a sensor that collects a user's bio-signal, and a dock that is installed on a body-wearable and/or body-attachable product and has a space for mounting the sensor, in which the sensor and the dock are detachable and attachable to each other using magnetism.

15 Claims, 9 Drawing Sheets

(52) U.S. Cl.
CPC ................. *A61B 2560/0204* (2013.01); *A61B 2560/0443* (2013.01); *A61B 2560/0456* (2013.01); *A61B 2562/08* (2013.01)

(58) Field of Classification Search
CPC ........ A61B 2560/0456; A61B 2562/08; A61B 5/01; A61B 5/02438; A61B 5/14552; A61B 5/02055; A61B 5/681; A61B 5/6801; A61B 5/0024; A61B 5/6802; A61B 5/6833; A61B 5/7275; A61B 2560/0214
See application file for complete search history.

(56) References Cited

U.S. PATENT DOCUMENTS

| | | | | |
|---|---|---|---|---|
| 2016/0192856 | A1 | 7/2016 | Lee | |
| 2018/0000405 | A1* | 1/2018 | Penders ............... | A61B 8/4416 |
| 2022/0265214 | A1* | 8/2022 | Jariwala ................. | A61B 5/296 |

FOREIGN PATENT DOCUMENTS

| | | | |
|---|---|---|---|
| WO | 2021/102050 | A1 | 5/2021 |
| WO | 2022/269259 | A1 | 12/2022 |

OTHER PUBLICATIONS

Extended European Search Report dated Jun. 12, 2024, issued in counterpart European Application No. 23219241.9 (7 pages).

* cited by examiner

BIO-SIGNAL MEASUREMENT DEVICE ATTACHABLE TO AND DETACHABLE FROM VARIOUS BODY-WEARABLE/BODY-ATTACHABLE PRODUCTS AND CONTROL METHOD THEREOF

BACKGROUND

1. Field

The present invention relates to a bio-signal measurement device attachable to and detachable from various body-wearable/body-attachable products, a control method thereof, and a computer program.

2. Description of Related Art

A bio-signal measurement device is a device used to measure and analyze various signals generated from a living body. Bio-signals are used to evaluate a health state, a disease, biological activity, and an emotional state of a user.

For example, an electrocardiogram signal measurement device is a device that measures bio-signals such as electrocardiograms by forming contact points with various body parts (chest, wrists, ankles, etc.) of a subject using patch-type electrodes, and may be used to predict or diagnose the occurrence of diseases such as arrhythmia and cardiac arrest by monitoring the bio-signals.

Recently, a wearable bio-signal measurement device that may be easily worn on a subject's body is being used in daily life.

The subject may easily measure bio-signals during his/her daily life using a wearable bio-signal measurement device, and medical staff may continuously receive the bio-signals measured by the wearable bio-signal measuring device to quickly diagnose and treat expected diseases and lower the risk of death.

However, the conventional wearable bio-signal measurement device is implemented in different types depending on a wearing location of a body (for example, a type worn on a subject's wrist is implemented as a smart watch, or a type worn around a subject's heart is implemented as an electrocardiogram patch), and therefore, has the disadvantage of being difficult to be modularized.

SUMMARY

The present invention provides a bio-signal measurement device attachable to and detachable from various body-wearable/body-attachable products and a bio-signal measurement method using the same.

According to an embodiment of the present invention, a bio-signal measurement device includes a sensor that collects a user's bio-signal, and a dock that is installed on a body-wearable and/or body-attachable product and has a space for mounting the sensor, in which the sensor and the dock are detachable and attachable to each other using magnetism.

The dock may have a guide member, which guides the sensor to be attached and detached in the space, protruding from an outer circumferential surface thereof.

One area of the guide member may be provided with a detachment groove for detaching the sensor.

The sensor may further include a control unit that detects whether the sensor is attached to or detached from the dock and controls the sensor to be turned on/off.

The sensor may further include a light emitting unit that emits light when attached to the space of the dock.

The sensor may further include a power supply unit that receives a user input for turning on/off an operation of the sensor or turning on/off the light emitting unit.

The sensor may include at least two of a heart rate sensing module, an electrocardiogram (ECG) sensing module, a body temperature sensing module, a galvanic skin response sensing module, an oxygen saturation (spO2) sensing module, a body fat sensing module, an electromyography (EMG) sensing module, and a motion sensing module.

The body-wearable product may include at least one of clothing, a band, a belt, and underwear, and the body-wearable product may include an electrode patch.

When the sensor is attached to the dock, the sensor may further include a control unit that determines product type information of a product on which the dock is installed.

The control unit may set an operation mode of the sensor to a mode corresponding to the product type information.

The operation mode may include at least two of a work risk determination mode, a sports risk determination mode, and a cardiovascular disease determination mode.

The bio-signal measurement device may further include a charger that charges the sensor, in which the charger may include a communication unit that transmits data stored in a storage unit of the sensor to an external device.

According to another embodiment of the present invention, a control method of a bio-signal measurement device including a sensor that collects a user's bio-signal, and a dock that is installed on a body-wearable and/or body-attachable product and has a space for mounting the sensor, the sensor and the dock being detachable and attachable to each other using magnetism, the control method includes: when the sensor is attached to the dock, determining product type information of a product on which the dock is installed, and setting an operation mode of the sensor to a mode corresponding to the product type information.

The sensor may include at least two of a heart rate sensing module, an electrocardiogram (ECG) sensing module, a body temperature sensing module, a galvanic skin response sensing module, an oxygen saturation (spO2) sensing module, a body fat sensing module, an electromyography (EMG) sensing module, and a motion sensing module.

The operation mode may include at least two of a work risk determination mode, a sports risk determination mode, and a cardiovascular disease determination mode.

The control method may further include controlling whether a plurality of sensing modules included in the sensor operate according to the set operation mode.

The bio-signal measurement device may further include a charger, and the control method may further include transmitting, by the charger, data stored in a storage unit of the sensor to an external device when the sensor is attached to the charger.

The body-wearable product may include at least one of clothing, a band, a belt, and underwear, and the body-wearable product may include an electrode patch.

The control method may further include detecting whether the sensor is attached to or detached from the dock and controlling the sensor to be turned on/off.

According to still another embodiment of the present invention, a non-transitory computer-readable recording medium recording a computer program performing a control method of a bio-signal measurement device that includes a sensor that collects a user's bio-signal, and a dock that is installed on a body-wearable and/or body-attachable product and has a space for mounting the sensor, the sensor and the dock being detachable and attachable to each other using magnetism, the control method including: when the sensor is attached to the dock, determining product type information of a product on which the dock is installed, and setting an operation mode of the sensor to a mode corresponding to the product type information.

DETAILED DESCRIPTION

Hereinafter, preferred embodiments of the present invention will be described in detail with reference to the accompanying drawings.

Figure 1:
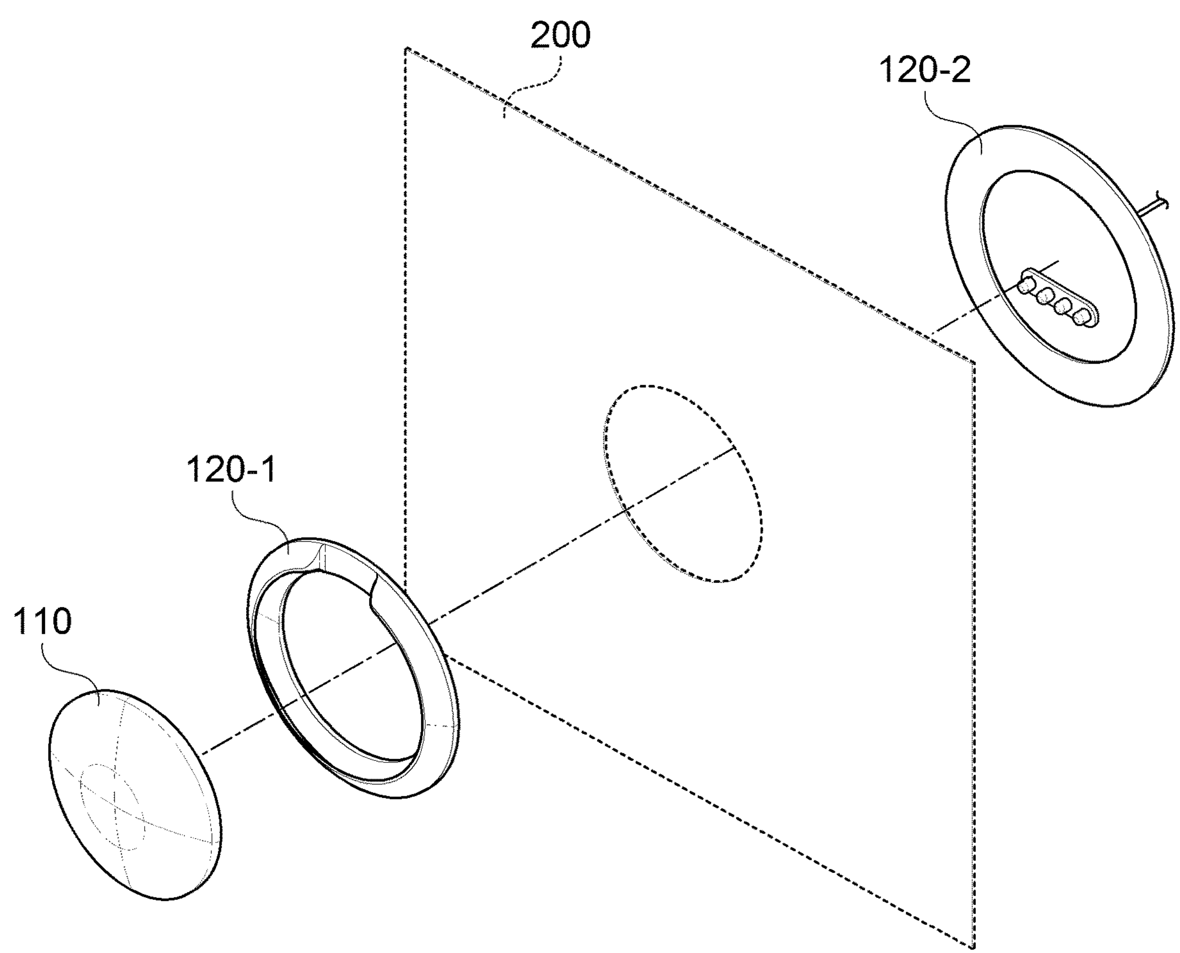
FIG. 1 is an exploded perspective view illustrating a bio-signal measurement device according to an embodiment of the present invention.

FIG. 1 is an exploded perspective view illustrating a bio-signal measurement device according to an embodiment of the present invention.

Referring to FIG. 1, a bio-signal measurement device 100 includes a bio-signal measurement sensor 110 that measures user's bio-signals such as electrocardiogram, heart rate, body temperature, motion, etc., and a dock 120 that serves as a stand for attachment and detachment of the bio-signal measurement sensor 110.

Specifically, the dock 120 includes a dock case 120-1 having a ring-shaped structure surrounding the bio-signal measurement sensor 110 to provide a space for the bio-signal measurement sensor 110 to be detached, and a dock base 120-2 that is coupled to a dock case 120-1 and supports the dock case 120-1 and is provided with a plurality of pogo pins to which the bio-signal measurement sensor 110 is electrically connected.

In exemplary embodiments, an edge portion of the dock base 120-2 may be an area for providing a space in which the dock case 120-1 is seated, and a middle portion located inside the edge portion of the dock base 120-2 may be an area for providing the space in which the plurality of pogo pins are installed.

In an embodiment, the bio-signal measurement sensor 110 and the dock base 120-2 may each be made of a magnetic material, and thus, the bio-signal measurement sensor 110 and the dock base 120-2 may be attached to and detached from each other by magnetism.

However, the concept of the present invention is not necessarily limited thereto, and the bio-signal measurement sensor 110 and the dock base 120-2 may not each be made of a magnetic material. That is, at least one of the bio-signal measurement sensor 110 and the dock base 120-2 may be made of a magnetic material. In this case, a magnet for providing magnetism is separately provided to attach the magnet to the other of the bio-signal measurement sensor 110 and the dock base 120-2, so the bio-signal measurement sensor 110 and the dock base 120-2 may be attached to and detached from each other by magnetism.

The coupling method of the dock case 120-1 and the dock base 120-2 is not particularly limited, and may be coupled to each other through chemical coupling or physical coupling.

Figure 2:
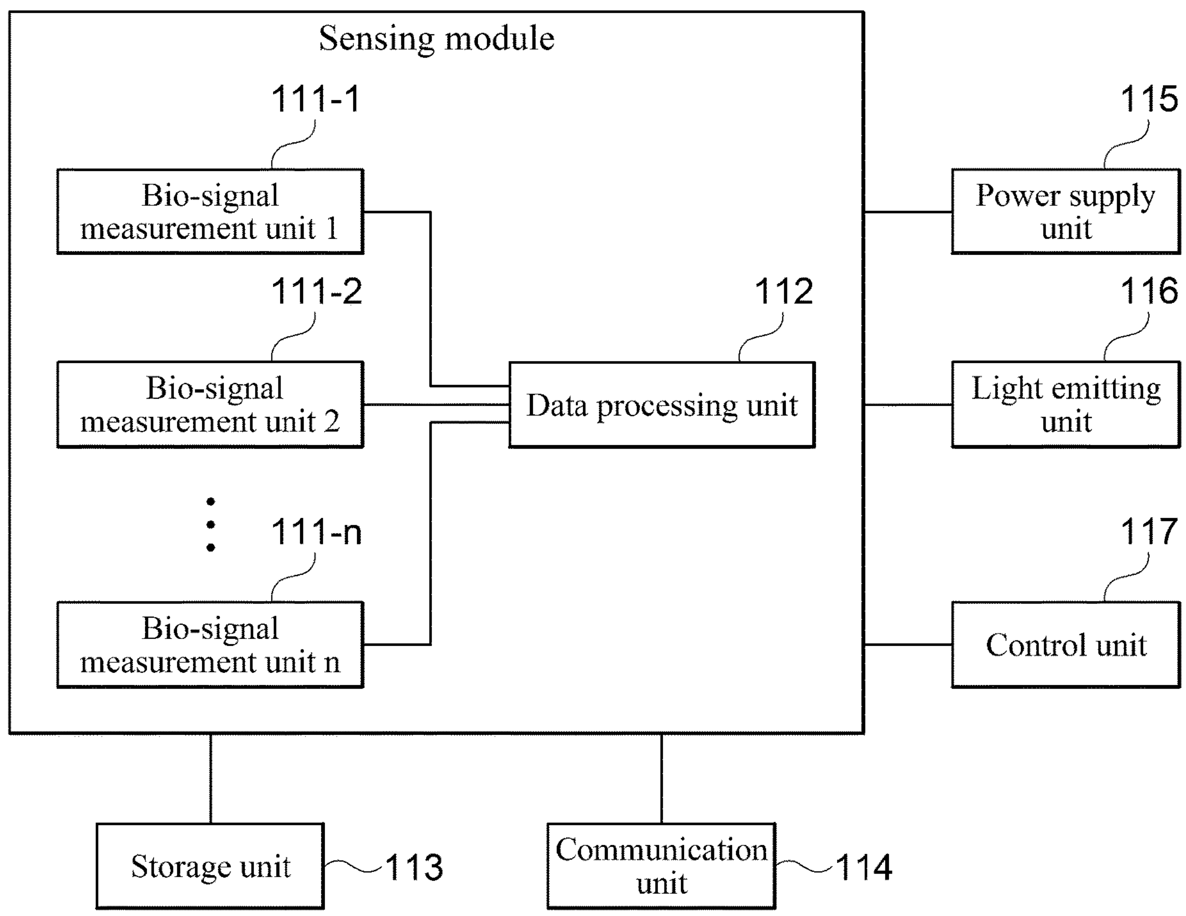
FIG. 2 is a block diagram illustrating a bio-signal measurement device according to an embodiment of the present invention.

Referring to FIG. 2, the bio-signal measurement sensor 110 according to an embodiment of the present invention will be described in more detail. Referring to FIG. 2, the bio-signal measurement sensor 110 may include all or part of a bio-signal measurement unit 111, a data processing unit 112, a storage unit 113, a communication unit 114, a power supply unit 115, a light emitting unit, and a control unit 117.

At least one of the bio-signal measurement units 111-1, 111-2 . . . 111-*n* (111) is provided to measure the user's bio-signal. Here, the bio-signal may include heart rate, electrocardiogram (ECG), body temperature, galvanic skin response, oxygen saturation (spO2), body fat, user motion, electromyography (EMG), etc.

The bio-signal measurement unit 111 may include all or part of a heart rate sensing module, an electrocardiogram (ECG) sensing module, a body temperature sensing module, a galvanic skin response sensing module, an oxygen saturation (spO2) sensing module, a body fat sensing module, an electromyography (EMG) sensing module, a motion sensing module, and a bioelectrical impedance analysis (BIA) sensing module, and measure various bio-signals of a subject. Here, the motion sensing module may be implemented as a gyro sensor, an acceleration sensor, a tilt sensor, etc.

The data processing unit 112 may process the signal measured by the bio-signal measurement unit 111 and store the processed signal in the storage unit 113. Here, the data processing unit 112 may be implemented using software, hardware, or a combination thereof. As an example, according to a hardware implementation, the data processing unit 112 may be implemented using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and electric units for performing other functions.

The communication unit 114 may perform a function for communications between a device and another electronic device. For example, the communication unit 110 may be implemented as a module that may perform near field communication (NFC) communication, beacon communication, Bluetooth communication, Zigbee communication, WI-FI communication, and Z-wave communication which are short-range wireless communications, and may be further implemented as a configuration that may perform LTE communication, 5G communication, radio-frequency identification (RFID) communication, and the like, that are long-range wireless communication.

Preferably, the communication unit 114 may be implemented as a module capable of performing Bluetooth low energy (BLE) communication.

The communication unit 114 may communicate with various terminal devices (not illustrated) such as smart watches and smartphones and/or a charger 300 and then transmit and receive various data such as biometric data and control commands.

The storage unit 113 may store various data generated in the bio-signal measurement unit 111.

Specifically, the bio-signal and biometric data measured by the bio-signal measurement unit 111 may be stored in the storage unit 113. In this case, the bio-signal and biometric data may be stored separately by measurement time, measurement object, product, etc.

The power supply unit 115 may include a battery and supply power to the bio-signal measurement sensor 110 to operate.

Here, the power supply unit 115 may be implemented as a predetermined button and receive a user input for turning on/off the operation of the bio-signal measurement sensor 110.

In addition, the button that performs the function of the power supply unit 115 may receive a user input for turning on/off the light emitting unit.

For example, when the power supply unit 115 is pressed for 3 seconds, the turn on/off operation of the bio-signal measurement sensor 110 may be controlled.

As another example, when the power supply unit 115 is pressed several times at intervals within 1 second, the turn on/off operation or the color change of the light emitting unit 116 in the bio-signal measurement sensor 110 may be controlled.

However, this is only an implementation example, and the bio-signal measurement sensor 110 may further include a separate input unit (not illustrated) that receives the user input, and the input unit (not illustrated) may receive the user input for turning on/off the operation and the user input for turning on/off the light emitting unit.

The light emitting unit 116 may emit various colors according to various operations of the bio-signal measurement sensor 110. Here, the light emitting unit 116 may include an LED capable of emitting various colors.

Specifically, the light emitting unit 116 may emit a specific color when the bio-signal measurement sensor 110 is attached to the space of the dock 120.

In addition, the light emitting unit 116 may change colors and emit light depending on the remaining battery in the bio-signal measurement sensor 110.

In addition, the light emitting unit 116 may emit a specific color depending on the operation status of the communication unit 114 within the bio-signal measurement sensor 110.

For example, when the communication unit 114 is transmitting and receiving biometric data to an external device (e.g., a wearable device), the light emitting unit 116 may blink red at predetermined intervals.

In this way, it may be guided for a user not to detach the bio-signal measurement sensor 110 while transmitting and receiving data.

The control unit 117 may control various operations of the bio-signal measurement sensor 110. Specifically, the control unit 117 may control all or part of the bio-signal measurement unit 111, the data processing unit 112, the storage unit 113, the communication unit 114, the power supply unit 115, and the light emitting unit 116.

In particular, the control unit 117 may detect whether the sensor 110 is attached to or detached from the dock 120 to control the bio-signal measurement sensor 110 to be turned on/off. In this case, the control unit 117 may detect contact between a connector of the bio-signal measurement sensor 110 and a connector of the dock 120 to detect whether the sensor 110 is attached to or detached from the dock 120.

In addition, the control unit 117 may acquire sensing data when the bio-signal measurement sensor 110 is attached to the dock 120, and determine product type information of a product on which the dock 120 is installed based on the acquired sensing data. Here, the sensing data may include a connector resistance value, location data of the bio-signal measurement sensor 110, user motion, the number of activated pogo pins, position patterns of the activated pogo pins, etc. In this case, the number of activated pogo pins refers to the number of pogo pins connected by the contact among the pogo pins, and the position patterns of the activated pogo pins may refer to the order in which the activated pogo pins are located among the pogo pins.

For example, when only two of the four pogo pins are activated, the control unit 117 may determine that the product type information of the product to which the bio-signal measurement sensor 110 is attached is sportswear clothing.

As another example, when only the first and fourth pogo pins of the four pogo pins are activated, the control unit 117 may determine that the product type information of the product to which the bio-signal measurement sensor 110 is attached is workwear clothing.

As another example, in the case of a user motion of shaking the bio-signal measurement sensor 110 once, the control unit 117 may determine the product type information of the product to which the bio-signal measurement sensor 110 is attached as the sportswear clothing, and in the case of a user motion of shaking the bio-signal measurement sensor 110 twice, the control unit 117 may determine that the product type information of the product to which the bio-signal measurement sensor 110 is attached is the workwear clothing.

In addition, the control unit 117 may determine the product type information of the product by considering a priority among various data in the sensing data. For example, the control unit 117 may determine the product type information of the product to which the signal measurement sensor 110 is attached by prioritizing the number of activated pogo pins or the position patterns of the activated pogo pin among various data in the sensing data.

In addition, the control unit 117 may set the operation mode of the bio-signal measurement sensor 110 to a mode corresponding to the product type information. Here, the operation mode may include at least two of a work risk determination mode, a sports risk determination mode, and a cardiovascular disease determination mode. In this case, the sensing module operated for each operation mode may be different.

For example, when the bio-signal measurement sensor 110 is attached to the dock 120 attached to sportswear, the control unit 117 may set the operation mode to the sports risk determination mode.

In addition, the control unit 117 may control an operation of a plurality of sensing modules included in the bio-signal measurement sensor according to the operation mode.

For example, when the mode of the bio-signal measurement sensor 110 is the sports risk determination mode, the control unit 117 may control the bio-signal measurement sensor 110 to measure a bio-signal through a heart rate sensing module, a body temperature sensing module, and a motion sensing module among various sensing modules.

Meanwhile, if additionally described with reference to FIG. 1, the dock 120 may be installed on various body-wearable and/or body-attachable products 200. A body-wearable product may be a product worn on a user's body, such as clothing, bands, belts, and underwear. In addition, the body-attachable product may be a product that is attached to the user's body, such as an electrode patch.

In this case, the dock 120 may be installed on various body-wearable and/or body-attachable products 200 in an attachable and detachable or fixed form.

Meanwhile, connectors may be formed on each of the bio-signal measurement sensor 110 and the dock 120. Specifically, a first connector may be formed in the bio-signal measurement sensor 110, and a second connector may be formed in the dock 120. Accordingly, various types of information may be exchanged between the connectors.

In addition, functions such as charging the bio-signal measurement sensor 110 or transmitting data to a speaker or PC may be used through the connector of the bio-signal measurement sensor 110.

Here, the first connector may be composed of a pogo pin connector (pogo pin connector/spring loaded pogo pin connector), more preferably a female connector of a magnetic pogo pin connector that is attachable and detachable using magnetism.

The second connector may be composed of the pogo pin connector, preferably a male connector of the magnetic pogo pin connector.

In this case, the number and locations of activated pogo pins in the male connector of the pogo pin connector may vary depending on the type of product.

For example, for the sportswear clothing, only two of the four pogo pins may be activated and two pogo pins may be deactivated; for the workwear clothing, only one of the four pogo pins may be activated and three pogo pins may be deactivated.

As another example, for the sportswear clothing, only the pogo pins at both ends of the four pogo pins may be activated.

In addition, the pogo pins in the second connector may each have different resistance values depending on the type of product.

Meanwhile, the dock 120 may be provided with a magnet, and the bio-signal measurement sensor 110 may be made of a magnetic material, so the bio-signal measurement sensor 110 may be attachable to and detachable from the dock 120 using magnetism.

That is, the bio-signal measurement sensor 110 and the dock 120 may have a structure that is attachable to and detachable from each other using magnetism.

Meanwhile, the connector formed on the dock 120 may be connected to the electrode formed on the product 200. For example, when the product 200 is implemented as clothing, electrodes may be formed on the inside of the clothing, and the electrodes may detect electrocardiogram signals by contacting a user's skin. This will be described in more detail with reference to FIGS. 3A to 3C.

Figure 3A:
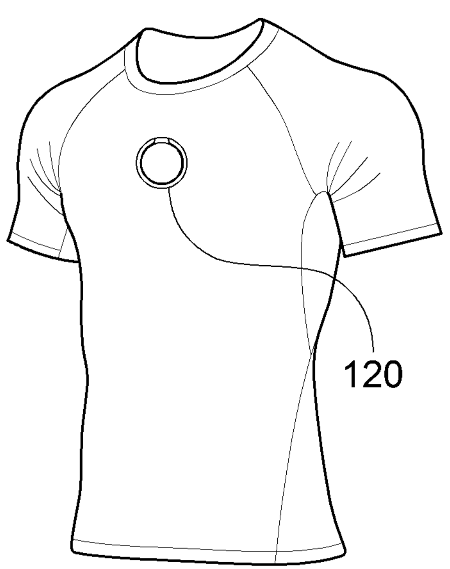
FIGS. 3A to 3C are diagrams illustrating the bio-signal measuring device according to an embodiment of the present invention and body-wearable clothing.
Figure 3B:
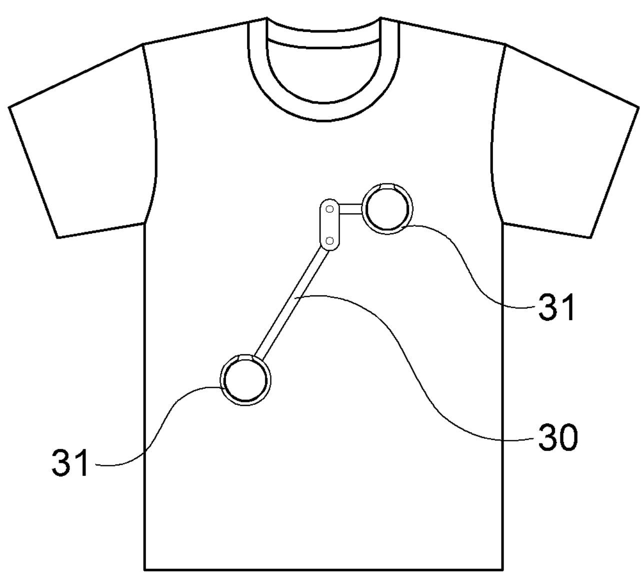
Figure 3C:
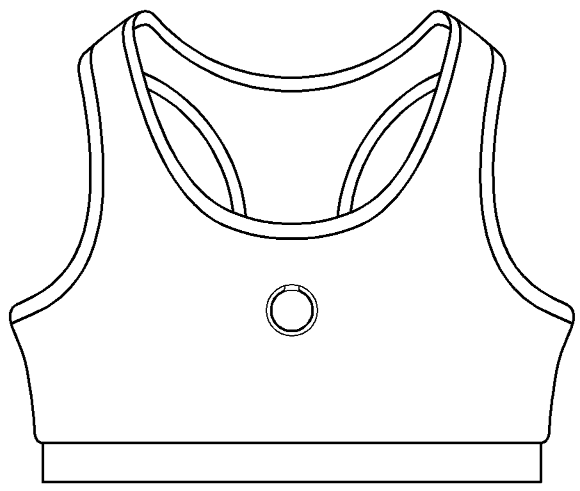

FIGS. 3A to 3C are diagrams illustrating clothing according to an embodiment of the present invention. Clothing may be classified into underwear essentially worn by a user in his/her daily life, activewear worn for activities, sportswear worn for exercising, and workwear worn while working.

FIG. 3A illustrates an outer side surface of the sportswear, and FIG. 3B illustrates an inner side surface of the sportswear.

Referring to FIG. 3A, a dock 120 may be installed on the outer side surface.

Referring to FIG. 3B, electrodes 31 for electrocardiogram measurement may be formed on an inner side surface, each electrode may be interconnected through a transmission line 30, and the electrocardiogram signal measured at each electrode 31 may be transmitted to the second connector through the transmission line 30. In this case, the second connector may be coupled to the dock 120 and electrically connected, and thus, the electrocardiogram signal measured through each electrode 31 may be transmitted to the dock 120 through the second connector.

FIG. 3C illustrates another type of sportswear, and the location of the dock 120 may vary depending on the type of product.

Figure 4:
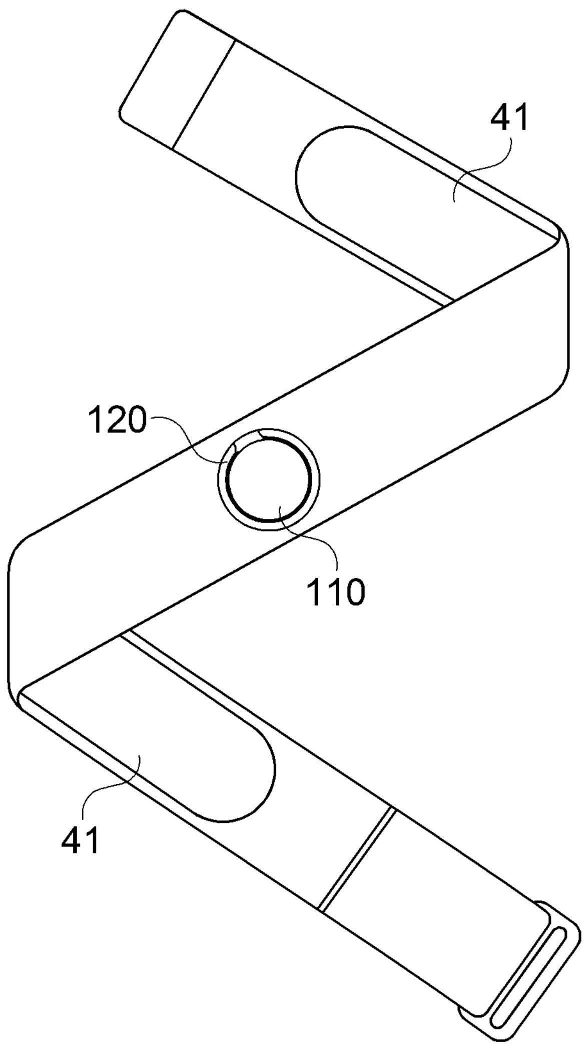
FIG. 4 is a diagram illustrating the bio-signal measurement device according to an embodiment of the present invention and a body-wearable band.

FIG. 4 is a view illustrating a band according to an embodiment of the present invention. The band is a band worn on the user's body and used to perform posture correction. The dock 120 may be installed on the outer side surface, and electrodes 41 for electrocardiogram measurement may be formed on the inner side surface in contact with the user's skin. Each electrode 41 is connected to each other through a transmission line (not illustrated), and the electrocardiogram signals measured at each electrode 41 may be transmitted to the second connector through a transmission line (not illustrated).

Figure 5:
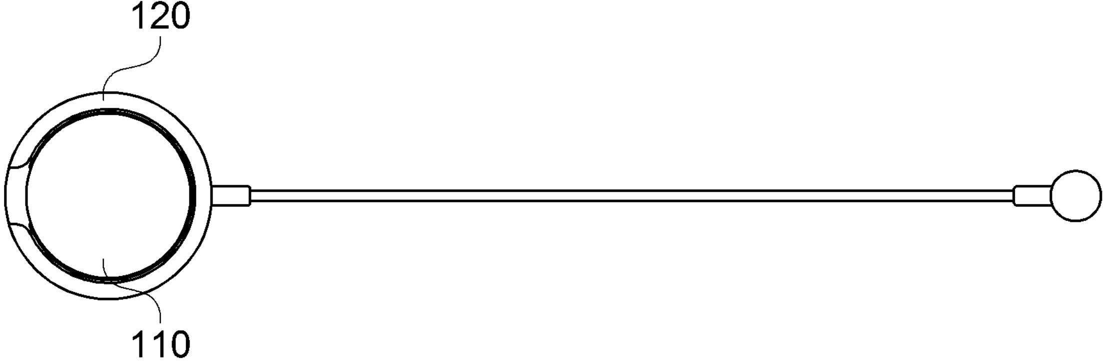
FIG. 5 is a diagram illustrating the bio-signal measurement device according to an embodiment of the present invention and electrode pad.

FIG. 5 is a diagram illustrating an electrode patch according to an embodiment of the present invention. The electrode patch is used by being attached to the user's body. The dock 120 may be installed on the outer side surface, and the electrodes (not illustrated) for the electrocardiogram measurement may be formed on the inner side surface in contact with the user's skin. Each electrode 41 is connected to each other through a transmission line (not illustrated), and the electrocardiogram signals measured at each electrode 41 may be transmitted to the second connector through a transmission line (not illustrated).

Meanwhile, the bio-signal measurement device 100 may include the charger 300 for charging the bio-signal measurement sensor 110, and this will be described with reference to FIG. 6.

Figure 6:
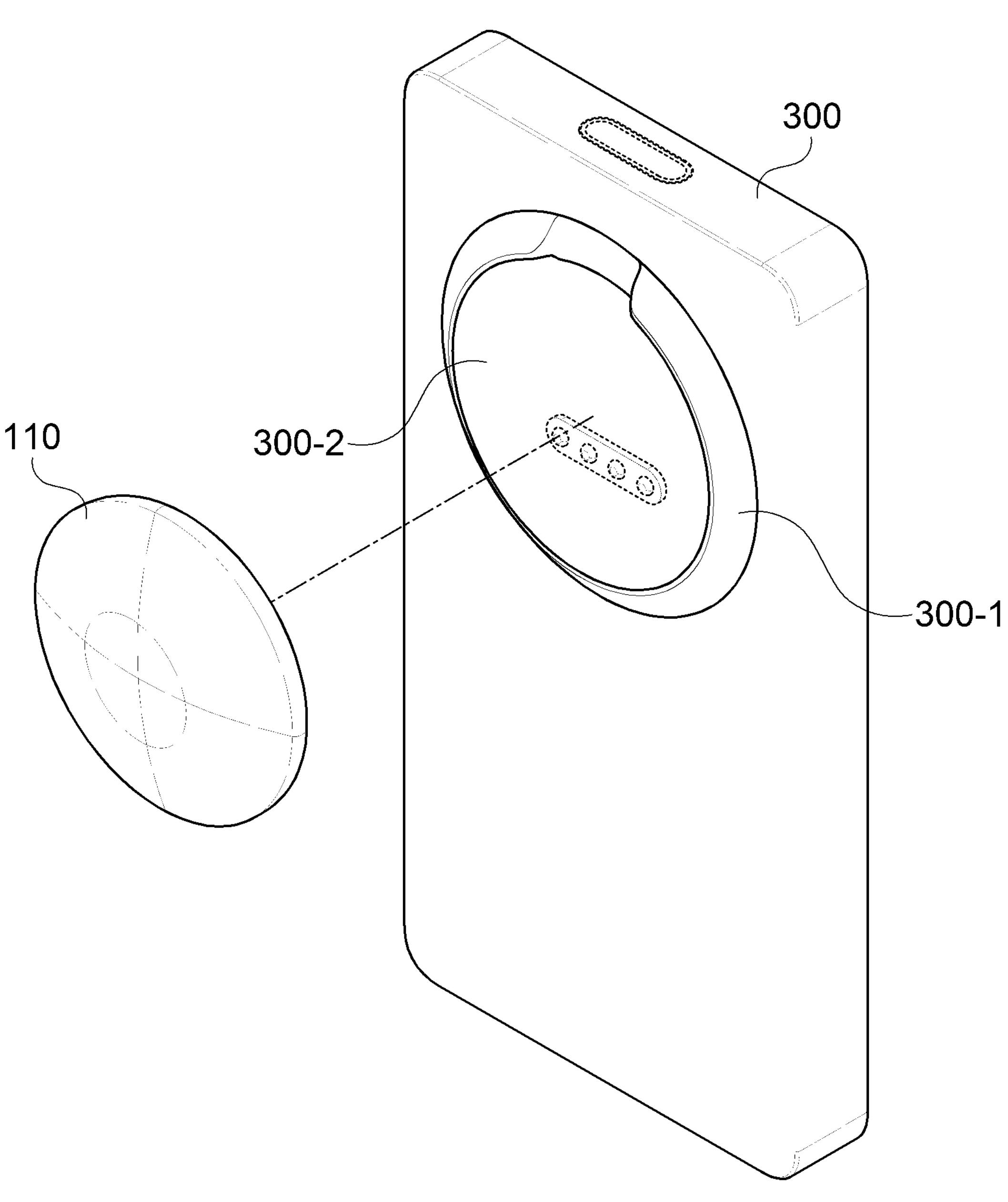
FIG. 6 is a perspective view illustrating a charger according to an embodiment of the present invention.

FIG. 6 is a perspective view illustrating the charger 300 according to an embodiment of the present invention. Referring to FIG. 6, a guide member that guides the attachment and detachment of the bio-signal measurement sensor 110 may be formed in the charger 300, and a detachment groove 300-2 may be formed for detachment of the bio-signal measurement sensor 110.

Here, the guide member 300-1 may have the same structure as the dock case 120-1 of the dock 120 illustrated in FIG. 1, and the detachment groove 300-2 may have the same structure as the dock base 120-2 of the dock 120 illustrated in FIG. 1.

In addition, similar to the attachment/detachment method of the dock 120, the bio-signal measurement sensor 110 and the detachment groove 300-2 may be attached to and detached from each other by magnetism.

In addition, a third connector for data transmission and power transmission may be formed on the inner side surface of the guide member 300-1, and the third connector may be composed of a pogo pin connector, preferably a male connector of a magnetic pogo pin connector.

In addition, when the bio-signal measurement sensor 110 is attached to the charger 300 through the guide member 300-1, the power unit (not illustrated) of the charger 300 may provide power to the bio-signal measurement sensor 110. In this case, power may be provided to the bio-signal measurement sensor 110 through the third connector, and if necessary, power may also be transmitted wirelessly to the bio-signal measurement sensor 110.

In addition, the communication unit (not illustrated) within the charger 300 may transmit data stored in the storage unit 113 of the bio-signal measurement sensor 110 to an external device.

For example, the communication unit within the charger 300 may transmit biometric data stored in the storage unit 113 of the bio-signal measurement sensor 110 to a biometric data management server.

Figure 7:
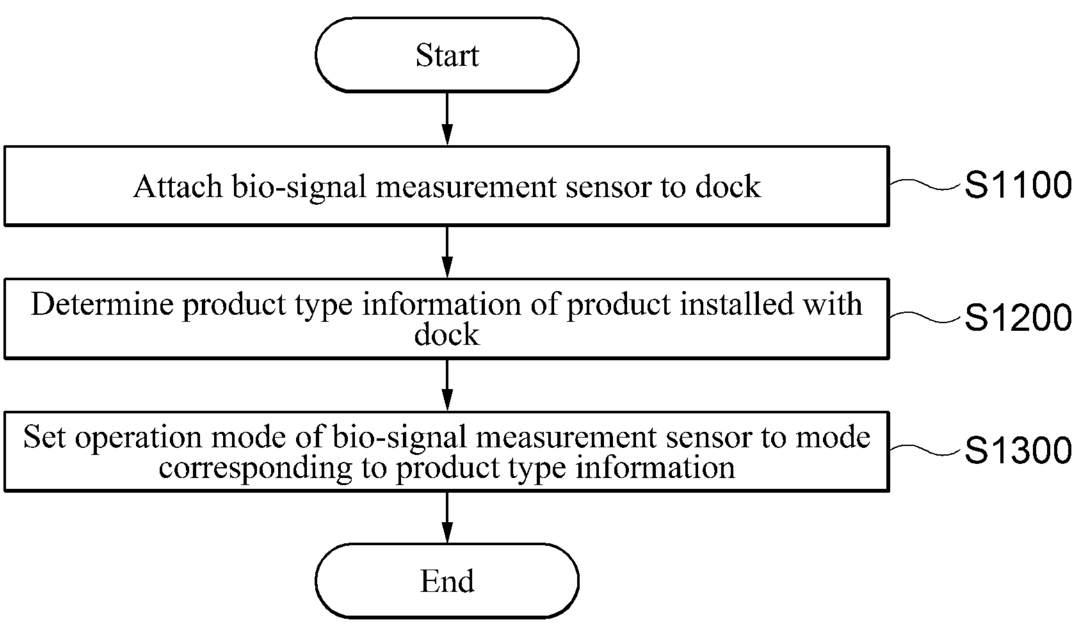
FIG. 7 is a flowchart illustrating a control method according to an embodiment of the present invention.

FIG. 7 is a flowchart illustrating a control method according to an embodiment of the present invention.

Referring to FIG. 7, the bio-signal measurement sensor 110 may be attached to the dock 120 (S1100). Specifically, the bio-signal measurement sensor 110 may be attached to the dock base 120-2 through the dock case 120-1.

When the bio-signal measurement sensor 110 is attached to the dock 120, the bio-signal measurement sensor 110 may determine the product type information of the product on which the dock 120 is installed (S1200). Specifically, the bio-signal measurement sensor 110 may acquire sensing data and determine the product type information of the product on which the dock 120 is installed based on the sensing data.

Next, the operation mode of the bio-signal measurement sensor 110 may be set to the mode corresponding to the product type information (S1300).

Next, the control method will be described in more detail with reference to FIG. 8.

Figure 8:
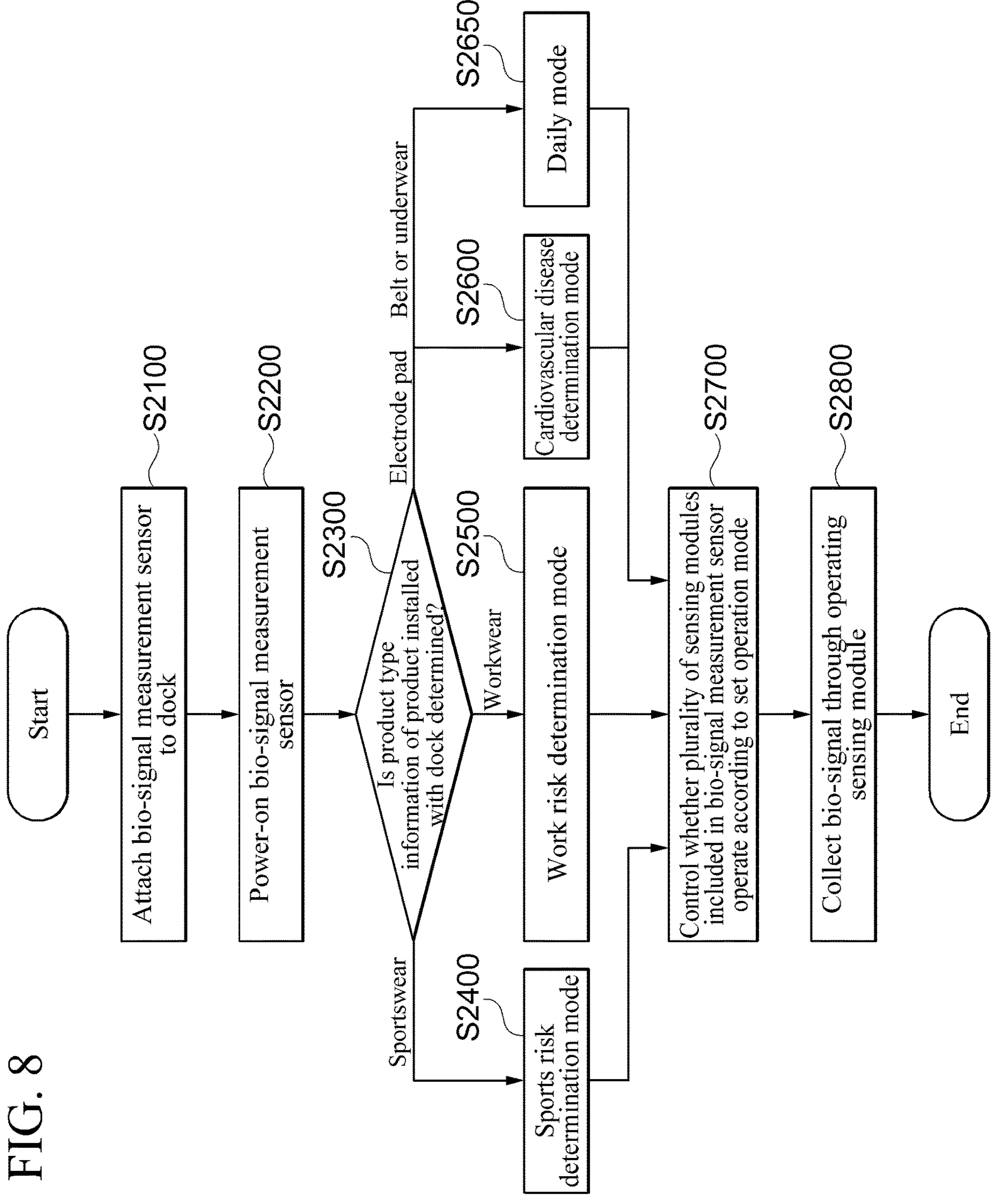
FIG. 8 is a flowchart illustrating in more detail the control method according to an embodiment of the present invention.

FIG. 8 is a flowchart illustrating in more detail the control method according to an embodiment of the present invention.

Referring to FIG. 8, when the bio-signal measurement sensor 110 is attached to the dock 120 (S2100), the bio-signal measurement sensor 110 may be powered-on (S2200).

Also, the bio-signal measurement sensor 110 that is powered-on may determine the product type information of the product on which the dock is installed (S2300).

In addition, the bio-signal measurement sensor 110 may set the operation mode of the sensor based on the product type information.

Specifically, when the product type is determined to be sportswear or a band, the bio-signal measurement sensor 110 may set the operation mode to the sports risk determination mode (S2400).

In addition, when the product type is determined to be workwear, the bio-signal measurement sensor 110 may set the operation mode to the work risk determination mode (S2500).

In addition, when the product type is determined to be the electrode pad, the bio-signal measurement sensor 110 may set the operation mode to the cardiovascular disease determination mode (S2600).

In addition, when the product type is determined to be a belt or underwear, the bio-signal measurement sensor 110 may set the operation mode to the normal mode (S2650).

Next, the bio-signal measurement sensor 110 may control whether the plurality of sensing modules included in the bio-signal measurement sensor are operated according to the set operation mode (S2700).

For example, when the operation mode of the sensor 110 is the sports risk determination mode, the bio-signal measurement sensor 110 may activate at least heart rate sensing module, body temperature sensing module, body fat sensing module, and motion sensing module among various sensing modules to measure the bio-signal. Here, the heart rate, body temperature, body fat, and motion data measured through the activated sensing module may be used to determine the risk of subject's sports activities (e.g., cardiac arrest, body temperature, activity level, etc.).

As another example, when the operation mode of the sensor 110 is the work risk determination mode, the bio-signal measurement sensor 110 may activate at least a motion sensing module and an electrocardiogram (ECG) sensing module among various sensing modules to measure the bio-signal. Here, the motion data measured through the activated sensing modules may be used to determine whether work should continue through the risk (e.g., falling, etc.) of subject's work activities and the electrocardiogram change.

As another example, when the operation mode of the sensor 110 is the cardiovascular disease determination mode, the bio-signal measurement sensor 110 may activate at least the electrocardiogram (ECG) sensing module and the oxygen saturation (spO2) sensing module to measure the bio-signal. Here, the electrocardiogram data and oxygen saturation data measured through the activated sensing module may be used to determine the subject's cardiovascular disease.

As another example, when the operation mode of the sensor 110 is the daily mode, the bio-signal measurement sensor 110 may activate at least the electrocardiogram (ECG) sensing module and the body temperature sensing module to measure the bio-signal. Here, the electrocardiogram data and body temperature data measured through the activated sensing module may be used to monitor the subject's daily health state.

Next, the bio-signal measurement sensor 110 may collect the bio-signal through the activated sensing module and store the bio-signal (S2800). In this case, the bio-signal measurement sensor 110 may distinguish and store the bio-signal measured for each product.

According to the present invention described above, since the bio-signal measurement sensor may be attached to and detached from various body-wearable/attachable products (e.g., clothing, bands, belts, underwear, and electrode patches, etc.) depending on the type of products the subject is wearing, the type of bio-signals to be measured, the activity state of the subject, etc., it is possible to increase the convenience of measuring the bio-signals of the subject.

In addition, according to the present invention, since clothing, bands, belts, underwear, etc., should be worn during daily life or exercise, the subject can measure the bio-signals only when he or she is equipped with a bio-signal measurement sensor.

In addition, according to the present invention, the bio-signals can be continuously monitored by attachment to and detachment from various body wearable/attachable products, and thus, the subject's health can be managed more easily.

In addition, in the disclosure and the claims, terms such as "first", "second", "third", "fourth", and the like, if any, will be used to distinguish similar components from each other and be used to describe a specific sequence or a generation sequence, but is not necessarily limited thereto. It will be understood that these terms are compatible with each other under an appropriate environment so that exemplary embodiments of the present invention set forth herein may be operated in a sequence different from a direction illustrated or described herein. Similarly, when a method in the present invention is described as comprising a series of steps, the order of those steps presented herein is not necessarily the order in which those steps can be performed, and any described steps may be omitted and/or may be omitted herein. Any other steps not described herein could be added to the method. For example, the 'first' component may be named the 'second' component, and vice versa, without departing from the scope of the present invention.

In addition, in the disclosure and the claims, terms such as "left", "right", "front", "rear", "top", "bottom", "over", "under", and the like, if any, do not necessarily indicate relative positions that are not changed, but are used for explanation. It will be understood that these terms are compatible with each other under an appropriate environment so that exemplary embodiments of the present invention set forth herein may be operated in a direction different from a direction illustrated or described herein. A term "connected" used herein is defined as being directly or indirectly connected in an electrical or non-electrical scheme. Here, targets described as being "adjacent to" each other may physically contact each other, be close to each other, or be in the same general range or region, in a context in which the above phrase is used. Here, a phrase "in an exemplary embodiment" means the same exemplary embodiment, but is not necessarily limited thereto.

In addition, in the disclosure and the claims, terms such as "connected", "connecting", "linked", "linking", "coupled", "coupling", and the like, and various modifications of these terms may be used as the meaning including that one component is directly connected to another component or is indirectly connected to another component through the other component.

On the other hand, it should be understood that when one element is referred to as being "connected directly to" or "coupled directly to" another element, it may be connected to or coupled to another element without the other element interposed therebetween.

In addition, terms "module" and "unit" for components used in the present invention are used only in order to easily make the disclosure. Therefore, these terms do not have meanings or roles that distinguish from each other in themselves.

In addition, terms used in the present specification are for explaining exemplary embodiments rather than limiting the present invention. In the present specification, singular forms include plural forms unless the context clearly indicates otherwise. In the specification, it is to be noted that the terms "comprising" or "including," and the like, are not be construed as necessarily including several components or several steps described in the specification and some of the above components or steps may not be included or additional components or steps are construed as being further included.

Hereinabove, the present invention has been described with reference to exemplary embodiments. All exemplary embodiments and conditional illustrations disclosed in the present invention have been described to intend to assist in the understanding of the principle and the concept of the present invention by those skilled in the art to which the present invention pertains. Therefore, it will be understood by those skilled in the art to which the present invention pertains that the present invention may be implemented in modified forms without departing from the spirit and scope of the present invention.

Therefore, exemplary embodiments disclosed herein should be considered in an illustrative aspect rather than a restrictive aspect. The scope of the present invention should be defined by the claims rather than the above-mentioned description, and equivalents to the claims should be interpreted to fall within the present invention.

Meanwhile, the control method according to various exemplary embodiments of the present invention described above may be implemented as programs and be provided to servers or devices. Therefore, the respective apparatuses may access the servers or the devices in which the programs are stored to download the programs.

In addition, the methods according to various exemplary embodiments of the present invention described above may be implemented as programs and be provided in a state in which it is stored in various non-transitory computer-readable media. The non-transitory computer-readable medium is not a medium that stores data therein for a while, such as a register, a cache, a memory, or the like, but means a medium that semi-permanently stores data therein and is readable by an apparatus. In detail, the various applications or programs described above may be stored and provided in the non-transitory computer readable medium such as a compact disk (CD), a digital versatile disk (DVD), a hard disk, a Blu-ray disk, a universal serial bus (USB), a memory card, a read only memory (ROM), or the like.

According to the present invention, since the bio-signal measurement sensor may be attached to and detached from various body-wearable/attachable products (e.g., clothing, bands, belts, underwear, and electrode patches, etc.) depending on the type of products the subject is wearing, the type of bio-signals to be measured, the subject's activity state, etc., it is possible to increase the convenience of measuring the subject's bio-signals.

In addition, according to the present invention, since clothing, bands, belts, underwear, etc., should be worn during daily life or exercise, the subject can measure the bio-signals only when he or she is equipped with a bio-signal measurement sensor.

In addition, according to the present invention, the bio-signals can be continuously monitored by attachment to and detachment from various body wearable/attachable products, and thus, the subject's health can be managed more easily.

Although the exemplary embodiments of the present invention have been illustrated and described hereinabove, the present invention is not limited to the specific exemplary embodiments described above, but may be variously modified by those skilled in the art to which the present invention pertains without departing from the scope and spirit of the invention as claimed in the claims. These modifications should also be understood to fall within the technical spirit and scope of the present invention.

What is claimed is:

1. A bio-signal measurement device, comprising:

a sensor that collects a user's bio-signal; and a dock that is installed on a body-wearable and/or body-attachable product and has a space for mounting the sensor, wherein the body-wearable product includes at least one of clothing, a band, a belt, and underwear, wherein the body-attachable product includes an electrode patch, wherein the sensor comprises:

a control unit configured to, when the sensor is attached to the dock, determine product type information of a product on which the dock is installed, wherein the control unit is configured to:

set an operation mode of the sensor to a work risk determination mode when the product type is determined to be workwear among the clothing, set the operation mode of the sensor to a sports risk determination mode when the product type is determined to be sportswear among the clothing or the band, set the operation mode of the sensor to a cardiovascular disease determination mode when the product type is determined to be the electrode patch, and set the operation mode of the sensor to a daily mode when the product type is determined to be the belt or the underwear, wherein motion data measured through activated sensing modules among a plurality of sensing modules of the sensor in the work risk determination mode is used to determine a risk of work activities of the subject, and an electrocardiogram change is used to determine whether work should continue, wherein heart rate, body temperature, body fat, and motion data measured through activated sensing modules among a plurality of sensing modules of the sensor in the sports risk determination mode are used to determine a risk of sports activities of a subject, wherein electrocardiogram data and oxygen saturation data measured through activated sensing modules among a plurality of sensing modules of the sensor in the cardiovascular disease determination mode are used to determine a cardiovascular disease of the subject, wherein electrocardiogram data and body temperature data measured through activated sensing modules among a plurality of sensing modules of the sensor in the daily mode are used to monitor a daily health state of the subject, wherein the sensor and the dock are detachable and attachable to each other using magnetism, wherein the sensor stores bio-data measured for each body-wearable and/or body-attachable product separately, and the bio-signal measurement device further comprises a charger for charging the sensor, wherein the sensor and the charger are detachable and attachable to each other using magnetism, and when the sensor is attached to the charger, the charger provides power to the sensor and transmits data stored in a storage unit of the sensor to an external device.

2. The bio-signal measurement device of claim 1, wherein the dock has a guide member, which guides the sensor to be attached and detached in the space, protruding from an outer circumferential surface thereof.

3. The bio-signal measurement device of claim 2, wherein one area of the guide member is provided with a detachment groove for detaching the sensor.

4. The bio-signal measurement device of claim 1, wherein the control unit detects whether the sensor is attached to or detached from the dock and controls the sensor to be turned on/off.

5. The bio-signal measurement device of claim 1, wherein the sensor further includes a light emitting unit that emits light when attached to the space of the dock.

6. The bio-signal measurement device of claim 1, wherein the sensor further includes a power supply unit that receives a user input for turning on/off an operation of the sensor or turning on/off a light emitting unit.

7. The bio-signal measurement device of claim 1, wherein the sensor includes at least two of a heart rate sensing module, an electrocardiogram (ECG) sensing module, a body temperature sensing module, a galvanic skin response sensing module, an oxygen saturation (spO2) sensing module, a body fat sensing module, an electromyography (EMG) sensing module, and a motion sensing module.

8. The bio-signal measurement device of claim 1, wherein the control unit sets an operation mode of the sensor to a mode corresponding to the product type information.

9. The bio-signal measurement device of claim 8, wherein the operation mode includes at least two of the work risk determination mode, the sports risk determination mode, and the cardiovascular disease determination mode.

10. A control method of a bio-signal measurement device including a sensor that collects a user's bio-signal, and a dock that is installed on a body-wearable and/or body-attachable product and has a space for mounting the sensor, the sensor and the dock being detachable and attachable to each other using magnetism, the body-wearable product including at least one of clothing, a band, a belt, and underwear, and the body-attachable product including an electrode patch, the control method comprising:

when the sensor is attached to the dock, determining product type information of a product on which the dock is installed, setting an operation mode of the sensor to a mode corresponding to the product type information, setting an operation mode of the sensor to a work risk determination mode when the product type is determined to be workwear among the clothing, setting the operation mode of the sensor to a sports risk determination mode when the product type is determined to be sportswear among the clothing or the band, setting the operation mode of the sensor to a cardiovascular disease determination mode when the product type is determined to be the electrode patch, setting the operation mode of the sensor to a daily mode when the product type is determined to be the belt or the underwear, wherein motion data measured through activated sensing modules among a plurality of sensing modules of the sensor in the work risk determination mode is used to determine a risk of work activities of the subject, and an electrocardiogram change is used to determine whether work should continue, wherein heart rate, body temperature, body fat, and motion data measured through activated sensing modules among a plurality of sensing modules of the sensor in the sports risk determination mode are used to determine a risk of sports activities of a subject, wherein electrocardiogram data and oxygen saturation data measured through activated sensing modules among a plurality of sensing modules of the sensor in the cardiovascular disease determination mode are used to determine a cardiovascular disease of the subject, wherein electrocardiogram data and body temperature data measured through activated sensing modules among a plurality of sensing modules of the sensor in the daily mode are used to monitor a daily health state of the subject, wherein the sensor stores bio-data measured for each body-wearable and/or body-attachable product separately, and the bio-signal measurement device further comprises a charger for charging the sensor, wherein the sensor and the charger are detachable and attachable to each other using magnetism, and when the sensor is attached to the charger, the charger provides power to the sensor and transmits data stored in a storage unit of the sensor to an external device.

11. The control method of claim 10, wherein the sensor includes at least two of a heart rate sensing module, an electrocardiogram (ECG) sensing module, a body temperature sensing module, a galvanic skin response sensing module, an oxygen saturation (spO2) sensing module, a body fat sensing module, an electromyography (EMG) sensing module, and a motion sensing module.

12. The control method of claim 11, wherein the operation mode includes at least two of the work risk determination mode, the sports risk determination mode, and the cardiovascular disease determination mode.

13. The control method of claim 12, further comprising:
controlling whether a plurality of sensing modules included in the sensor operate according to the set operation mode.

14. The control method of claim 10, further comprising:
detecting whether the sensor is attached to or detached from the dock and controlling the sensor to be turned on/off.

15. A non-transitory computer-readable recording medium recording a computer program performing a control method of a bio-signal measurement device that includes a sensor that collects a user's bio-signal, and a dock that is installed on a body-wearable and/or body-attachable product and has a space for mounting the sensor, the sensor and the dock being detachable and attachable to each other using magnetism, the body-wearable product including at least one of clothing, a band, a belt, and underwear, and the body-attachable product including an electrode patch,
wherein the control method includes:
when the sensor is attached to the dock, determining product type information of a product on which the dock is installed,
setting an operation mode of the sensor to a mode corresponding to the product type information,
setting an operation mode of the sensor to a work risk determination mode when the product type is determined to be workwear among the clothing,
setting the operation mode of the sensor to a sports risk determination mode when the product type is determined to be sportswear among the clothing or the band,
setting the operation mode of the sensor to a cardiovascular disease determination mode when the product type is determined to be the electrode patch,
setting the operation mode of the sensor to a daily mode when the product type is determined to be the belt or the underwear,
wherein motion data measured through activated sensing modules among a plurality of sensing modules of the sensor in the work risk determination mode is used to determine a risk of work activities of the subject, and an electrocardiogram change is used to determine whether work should continue,
wherein heart rate, body temperature, body fat, and motion data measured through activated sensing modules among a plurality of sensing modules of the sensor in the sports risk determination mode are used to determine a risk of sports activities of a subject,
wherein electrocardiogram data and oxygen saturation data measured through activated sensing modules among a plurality of sensing modules of the sensor in the cardiovascular disease determination mode are used to determine a cardiovascular disease of the subject,
wherein electrocardiogram data and body temperature data measured through activated sensing modules among a plurality of sensing modules of the sensor in the daily mode are used to monitor a daily health state of the subject,
wherein the sensor stores bio-data measured for each body-wearable and/or body-attachable product separately, and
the bio-signal measurement device further comprises a charger for charging the sensor, wherein the sensor and the charger are detachable and attachable to each other using magnetism, and when the sensor is attached to the charger, the charger provides power to the sensor and transmits data stored in a storage unit of the sensor to an external device.

* * * * *